United States Patent
Matsuo et al.

(10) Patent No.: US 7,829,294 B2
(45) Date of Patent: Nov. 9, 2010

(54) ANTI-HUMAN SOLUBLE FIBRIN MONOCLONAL ANTIBODY AND IMMUNOLOGICAL ASSAY METHOD USING THE ANTIBODY

(75) Inventors: Masanao Matsuo, Naka-gun (JP); Hiroyuki Ebinuma, Ryugasaki (JP); Osamu Miyazaki, Naka-gun (JP); Kyoko Tanaka, Naka-gun (JP); Akiko Suzuki, Ryugasaki (JP)

(73) Assignee: Daiichi Pure Chemicals Co., Ltd., Tokyo (JP)

( * ) Notice: Subject to any disclaimer, the term of this patent is extended or adjusted under 35 U.S.C. 154(b) by 41 days.

(21) Appl. No.: 11/722,998

(22) PCT Filed: Dec. 27, 2005

(86) PCT No.: PCT/JP2005/023848

§ 371 (c)(1),
(2), (4) Date: Jun. 28, 2007

(87) PCT Pub. No.: WO2006/070776

PCT Pub. Date: Jul. 6, 2006

(65) Prior Publication Data

US 2008/0009077 A1    Jan. 10, 2008

(30) Foreign Application Priority Data

Dec. 28, 2004    (JP) .............................. 2004-378598

(51) Int. Cl.
| | |
|---|---|
| G01N 33/543 | (2006.01) |
| G01N 33/573 | (2006.01) |
| G01N 33/577 | (2006.01) |
| C07K 16/36 | (2006.01) |
| C12N 5/20 | (2006.01) |
| C12P 21/08 | (2006.01) |

(52) U.S. Cl. .................. 435/7.1; 435/7.4; 435/7.92; 435/7.93; 435/7.94; 435/7.95; 435/13; 435/70.21; 435/452; 435/331; 435/337; 436/518; 436/548; 436/69; 530/388.25; 530/391.1

(58) Field of Classification Search ................. 435/7.1, 435/7.4, 7.92, 7.93, 7.94, 7.95, 13, 70.21, 435/452, 331, 337; 436/518, 548, 69; 530/388.25, 530/391.1

See application file for complete search history.

(56) References Cited

U.S. PATENT DOCUMENTS

| | | | |
|---|---|---|---|
| 5,099,004 A | | 3/1992 | Nieuwenhuizen |
| 5,120,834 A | * | 6/1992 | Gargan et al. .......... 530/388.25 |
| 5,487,892 A | * | 1/1996 | Gargan .................... 424/145.1 |
| 5,821,068 A | * | 10/1998 | Soe et al. .................. 435/7.21 |
| 5,843,690 A | * | 12/1998 | Gargan ........................ 435/13 |
| 6,451,545 B2 | * | 9/2002 | Tanaka et al. ................ 435/7.2 |

FOREIGN PATENT DOCUMENTS

| | | |
|---|---|---|
| EP | 0 922 761 A1 | 6/1999 |
| JP | 8 301900 | 11/1996 |
| JP | 2004-053359 | 2/2004 |
| WO | WO 95/12617 | 5/1995 |
| WO | WO 95/22986 | 8/1995 |
| WO | WO 98/59047 | 12/1998 |

OTHER PUBLICATIONS

Sobel, J. H. et al.,"The Development of Assays for the Detection of Fibrin(ogen)olysis Based on COOH-Terminal Aα Chain Epitopes", Blood, vol. 84. No. 2, p. 535-546, 1994.
Ehrlich, P. H. et al.,"Monoclonal Antibodies to α -Chain regions of Human Fibrinogen That Participate in Polymer Formation", Biochemistry, vol. 22, No. 18, pp. 4184-4192, 1983.
Mitkevich, O. V. et al.,"Coagulation Factor XIIIa Undergoes a Conformational Change Evoked by Glutamine Substrate. Studies on Kinetics of Inhibition and Binding of XIIIa by a Cross-Reacting Antifibrinogen Antibody", The Journal of Biological Chemistry, vol. 273, No. 23, pp. 14387-14391, 1998.
Weisel, J. W. et al.,"The Structure and Function of the α C Domains of Fibrinogen", Annals New York Academy of Science, vol. 936, pgs. 312-327, 2001.
Medved, L. et al.,"Conformational Changes Upon Conversion of Fibrinogen into Fibrin. The Mechanisms of Exposure of Cryptic Sites", vol. 936, pp. 185-204, 2001.
Hamano, A. et al.,"A Novel Monoclonal Antibody to Fibrin Monomer and Soluble Fibrin for the Detection of Soluble Fibrin in Plasma", Clinical Chemical Acta, vol. 318, pp. 25-32, 2002.
Soe, G. et al.,"A Monoclonal Antibody That Recognizes a Neo-Antigen Exposed in the E Domain of Fibrin Monomer Complexed with Fibrinogen or its Derivatives: its Application to the Measurement of Soluble Fibrin in Plasma", Blood, vol. 88, No. 6, pp. 2109-2117, 1996.
Veklich, Y. I. et al.,"Carboxyl-terminal Portions of the α Chains of Fibrinogen and Fibrin", The Journal of Biological Chemistry, vol. 268, No. 18, pp. 13577-13585, 1993.
Ursula Scheefers-Borchel, et al., "Discrimination between fibrin and fibrinogen by a monoclonal antibody against a synthetic peptide", Proc. Natl. Acad. Sci. USA, vol. 82, Oct. 1985, pp. 7091-7095.
Sanjeev Raut, et al., "Characterisation of the chains of human fibrinogen isolated by perfusion chromatography using fibrin specific monoclonal antibodies", Thrombosis Research, vol. 79, No. 4, Aug. 15, 1995, XP-002518964, pp. 405-413.

(Continued)

Primary Examiner—Shafiqul Haq
Assistant Examiner—James L Grun
(74) Attorney, Agent, or Firm—Oblon, Spivak, McClelland, Maier & Neustadt, L.L.P.

(57) ABSTRACT

The present invention is directed to a monoclonal antibody against a soluble fibrin, which specifically recognizes a conformation-changed site newly occurred in a C-terminal region of an Aα-chain of the soluble fibrin formed through thrombin digestion of fibrinogen. The present invention is also directed to a hybridoma which produces the antibody, an immunological assay method employing the antibody, and a method for evaluating hypercoagulability in a test sample by measuring the soluble fibrin level in the sample with the assay method. Through employment of the monoclonal antibody of the present invention, soluble fibrin on which plasmin has not acted, which reflects exclusively initial hypercoagulability, can be specifically detected.

17 Claims, 3 Drawing Sheets

OTHER PUBLICATIONS

P. E. Gargan, et al., "A Monoclonal Antibody which Recognises an Epitopic Region Unique to the Intact Fibrin Polymeric Structure", International Journal of Fibrinolysis, vol. 7, No. 4, Jul. 1, 1993, XP-002059009, pp. 275-283.

O. V. Mitkevich, et al., "Monoclonal antibody directed to a fibrinogen Aα #529-539 epitope inhibits α-chain crosslinking by transglutaminases", Blood Coagulation & Fibrinolysis, vol. 7, No. 1, XP-008103616, Jan. 1996, pp. 85-92.

Akiko Suzuki, et al., "The monoclonal antibody that recognizes an epitope in the C-terminal region of the fibrinogen α-chain reacts with soluble fibrin and fibrin monomer generated by thrombin but not with those formed as plasmin degradation products", Thrombosis Research, vol. 121, No. 3, XP-022414052, Jan. 1, 2007, pp. 377-385.

P. M. Tymkewycz, et al., "Generation and partial characterization of five monoclonal antibodies with high affinities for fibrin", Blood Coagulation and Fibrinolysis, vol. 4, No. 2, XP-008103731, Apr. 1993, pp. 211-221.

* cited by examiner

ANTI-HUMAN SOLUBLE FIBRIN MONOCLONAL ANTIBODY AND IMMUNOLOGICAL ASSAY METHOD USING THE ANTIBODY

TECHNICAL FIELD

The present invention relates to a monoclonal antibody against a soluble fibrin, which does not react with fibrinogen but specifically recognizes a conformation-changed site newly occurred in a C-terminal region of an Aα-chain of the soluble fibrin formed through thrombin digestion of fibrinogen. The monoclonal antibody specifically detects the soluble fibrin without detecting a plasmin-digested soluble fibrin or cross-linked fibrin-degradation products because the conformation-changed site recognized by the monoclonal antibody is cleaved from the soluble fibrin through the plasmin digestion and thereby the monoclonal antibody loses its reactivity with the plasmin-digested soluble fibrin. The present invention also relates to an immunological assay method employing the monoclonal antibody. The present invention further relates to a method for evaluating hypercoagulability in a test sample by measuring the soluble fibrin level in the sample with the immunological assay method.

BACKGROUND ART

Detection of a molecular marker formed in the blood in response to activation of the coagulation-fibrinolytic system is an important factor for the early diagnosis of disseminated intravascular coagulation (DIC) syndrome, as well as checking of condition thereof. Particularly, soluble fibrin monomer complex (SFMC) has been clinically employed as a marker for detecting initial hypercoagulability.

Thrombin, which has been formed through activation in a blood vessel, cuts the N-terminal of an Aα-chain of fibrinogen to thereby form a desAA fibrin monomer, and further cuts the N-terminal of a Bβ-chain thereof to thereby form a desAABB fibrin monomer. The thus-formed fibrin monomer forms a complex with fibrinogen or others in the blood, and the complex (i.e., SFMCs) circulates in the blood. As has been known, thrombogenesis can be detected in an early stage through detecting the SFMC.

Hitherto, a variety of specific antibodies and immunological assay methods for detecting SFMC have been reported. For example, G. Soe et al. have reported an IF-43 antibody as a monoclonal antibody which recognizes a conformation-change occurring in the E domain during formation of a fibrin-fibrinogen complex from a fibrin monomer and fibrinogen. The epitope recognized by the IF-43 antibody is present at an amino acid sequence of the 17th to 78th amino acid residues in the N-terminal region of the Aα chain (SEQ ID NO: 1). The IF-43 antibody is characterized in that it does not act on fibrinogen, fibrin monomer, or fibrinogen-degradation products by plasmin or fibrin-degradation products by plasmin, and thus reflects the blood coagulation system; WO95/012617 and Soe, et al., Blood 88: 2109-2117 (1996).

However, a soluble fibrin assay reagent employing the IF-43 antibody (Iatro SF, Iatron) is known to act on a complex formed through reaction between fibrin monomer-degradation products by plasmin (fibrin fragment X, Y, or E) and fibrinogen, as well as on complex formed through reaction between fibrin monomer-degradation products by plasmin and fibrinogen-degradation products by plasmin (fragment X, Y, or D); JP (kokai) 2004-53359. Thus, since the IF-43 antibody also acts on the plasmin-digested soluble fibrin, the antibody cannot be considered as an antibody reflecting exclusively the coagulation system.

Also, an antibody which recognizes an amino acid sequence in the N-terminal region of the fibrinogen Aα chain (SEQ ID NO: 1) which is formed by cutting the Aα chain with thrombin has been reported. Specifically, Scheefers-Borchell et al. previously produced an antibody specific to soluble fibrin through immunization with a synthetic hexapeptide GPRVVE (SEQ ID NO: 2), which is identical to the amino acid sequence of the N-terminal region of fibrin, Scheefers-Borchell, et al., PNAS 82: 7091-7095 (1985). A. Hamano et al. previously produced an antibody (F405) specific to soluble fibrin using a fibrin monomer prepared by treating fibrinogen with batroxobin, as an immunogen; WO98/59047 and Hamano, et al., Clin. Chim. Acta 318: 25-32 (2002).

However, since the epitope recognized by these antibodies is an N-terminal amino acid sequence site which is formed through an action of thrombin on the Aα chain, these antibodies are considered to act on fibrin monomer-degradation products by plasmin, complexes thereof, and XDP fractions (DY, DXD, etc., cross-linked fibrin-degradation products by plasmin). Therefore, these antibodies are considered not to exclusively reflect the coagulation system, but to reflect both the coagulation and the fibrinolytic systems.

Furthermore, a monoclonal antibody which reacts with a peptide formed of the amino acid sequence of the 148th to 161st amino acid residues of a fibrinogen Aα chain has been reported; Japan (kokai) 2-028197. Since the recognition site of the antibody is not in the C-terminal side of the Aα chain (SEQ ID NO: 1) which is digested with plasmin, the antibody is considered to react with plasmin-digested soluble fibrin or cross-linked fibrin-degradation products by plasmin. Thus, the antibody cannot be considered as an antibody reflecting exclusively the coagulation system.

As described above, in many cases, conventional antibodies against a soluble fibrin formed through hypercoagulability also recognize a plasmin-digested soluble fibrin or cross-linked fibrin-degradation products by plasmim formed through the fibrinolytic system. Hitherto, no antibody has been known that specifically recognizes soluble fibrin on which plasmin has not acted, and no method has been reported that reflects exclusively the coagulation system.

[Patent Document 1] International Patent Publication No. 95/012617 Pamphlet

[Patent Document 2] Japanese Patent Application Laid-Open (kokai) No. 2004-53359

[Patent Document 3] International Patent Publication No. 98/59047 Pamphlet

[Patent Document 4] Japanese Patent Application Laid-Open (kokai) No. 2-028197

[Non-Patent Document 1] G. Soe., et al, Blood. 88, 2109-2117, 1996.

[Non-Patent Document 2] U. SCHEEFERS-BORCHEL et al, Proc. Natl. Acad. Sci. USA. 82, 7091-7095, 1985.

[Non-Patent Document 3] A. Hamano et al, Clinica Chimica Acta. 318, 25-32, 2002.

DISCLOSURE OF THE INVENTION

Problems to be Solved by the Invention

Thus, an object of the present invention is to provide a monoclonal antibody which reflects initial hypercoagulability and can specifically measure soluble fibrin on which plasmin has not acted; a hybridoma which can produce the monoclonal antibody; an immunological assay method for measuring the soluble fibrin employing the monoclonal antibody; and a method for evaluating hypercoagulability in a test sample through measuring the soluble fibrin level in the sample with the immunological assay method.

Means for Solving the Problems

The present inventors have carried out extensive studies in order to solve the aforementioned problems, and have found a monoclonal antibody which specifically recognizes a conformation-changed site newly occurred in a C-terminal region of an Aα-chain of a soluble fibrin formed through thrombin digestion of fibrinogen. The monoclonal antibody loses its reactivity with a plasmin-digested soluble fibrin when the site recognized by the antibody is cleaved from the soluble fibrin through plasmin digestion. The inventors have also found that plasma soluble fibrin on which plasmin has not acted can be specifically measured through employment of the antibody. The present invention has been accomplished on the basis of these findings.

Accordingly, the present invention provides a monoclonal antibody against a soluble fibrin, wherein the antibody specifically recognizes a conformation-changed site newly occurred in a C-terminal region of an Aα-chain of the soluble fibrin formed through thrombin digestion of a fibrinogen, wherein the site is cleaved from the soluble fibrin through plasmin digestion.

The present invention also provides a hybridoma which produces the aforementioned monoclonal antibody.

The present invention also provides an immunological assay method for measuring a soluble fibrin in a test sample, wherein the method comprises reacting the monoclonal antibody with the sample.

The present invention also provides a reagent for measuring a soluble fibrin, containing the monoclonal antibody.

The present invention also provides a method for evaluating hypercoagulability in a test sample, which comprises measuring the soluble fibrin level in the sample with the immunological assay method.

Effects of the Invention

The monoclonal antibody of the present invention can specifically recognize soluble fibrin on which plasmin has not acted, without recognizing plasmin-digested soluble fibrin or cross-linked fibrin-degradation products by plasmin. Thus, through employment of the monoclonal antibody of the present invention, initial hypercoagulability can be rapidly detected at high sensitivity.

BEST MODES FOR CARRYING OUT THE INVENTION

Figure 1:
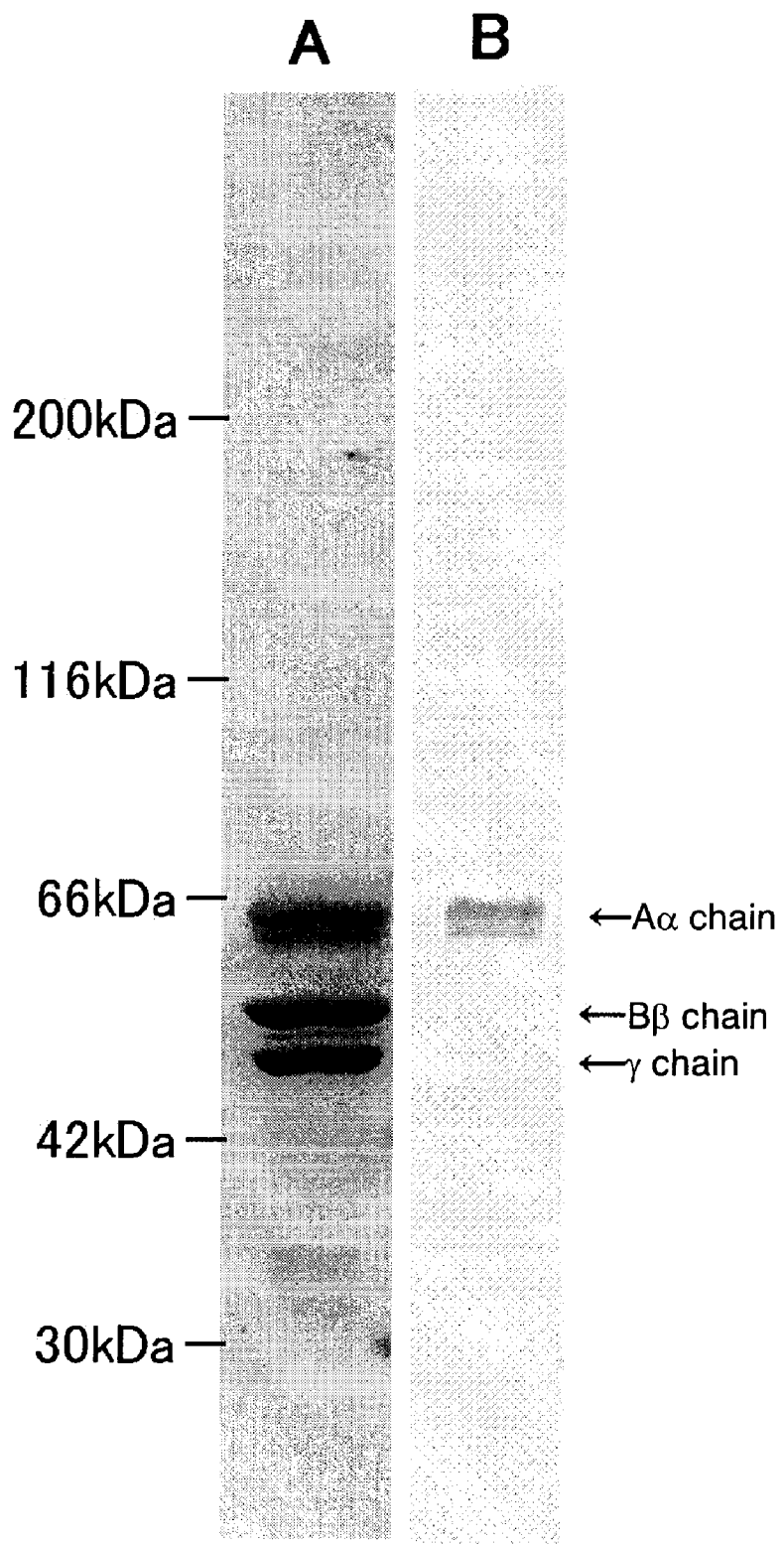
[FIG. 1] Analytical results for reactivity of J2-23 antibody with fibrinogen treated under reducing conditions, which was obtained in Example 3 (A: CBB staining, B: Western blotting).

As used herein, the term "soluble fibrin" collectively refers to a fibrin monomer (a desAA fibrin monomer or a desAABB fibrin monomer) and a fibrin monomer complex (a fibrin polymer, a fibrin monomer-fibrinogen complex, a fibrin monomer-FDP complex, or a complex of a fibrin monomer and other proteins in the body).

A characteristic feature of the monoclonal antibody of the present invention resides in that the antibody acts on the aforementioned soluble fibrin but does not act on fibrinogen, or fibrin monomer-degradation products by plasmin or cross-linked fibrin-degradation products by plasmin.

An epitope for the monoclonal antibody of the present invention is present at a conformation-changed site which is newly occurred in the C-terminal region of the Aα-chain of the soluble fibrin formed through thrombin digestion of fibrinogen and cleaved from the soluble fibrin through plasmin digestion. When the soluble fibrin is digested with plasmin, the recognition function of the monoclonal antibody for the plasmin-digested soluble fibrin is lost. Specifically, the epitope is present in, among fragments formed through plasmin digestion of fibrinogen, a C-terminal fragment of an Aα-chain of fibrinogen. The epitope is present at a digested peptide fragment having a molecular weight of about 16 kDa, wherein its N-terminal end corresponds to the 425th amino acid residue of the Aα-chain.

More specifically, the epitope is present at a polypeptide having an amino acid sequence consisting of the 502nd to 521st amino acid residues in the fibrinogen Aα-chain. No particular limitation is imposed on the type of the monoclonal antibody of the present invention, so long as the antibody recognizes a polypeptide having an amino acid sequence consisting of the 502nd to 521st amino acid residues in the fibrinogen Aα-chain.

Thus, there has never been known a monoclonal antibody which does not react with fibrinogen itself but recognizes a conformation-changed site which is newly occurred in the C-terminal region of the Aα-chain of the soluble fibrin formed through thrombin digestion of fibrinogen and cleaved from the soluble fibrin through plasmin digestion. Thus, the monoclonal antibody of the present invention is a novel monoclonal antibody. Hitherto, any conformation-changes in the C-terminal region of the Aα-chain of soluble fibrin have not been elucidated clearly. However, according to a report by Y. I. Veklich et al. (J. Bio. Chem., 1993; 268, 13577-13585), a fragment cleaved from the Aα-chain by plasmin is a digestion fragment having a molecular weight of 40 kDa in which its N-terminal end corresponds to the 220th amino acid residue of the Aα-chain, which indicates that the recognition site for the monoclonal antibody of the present invention is included in the fragment cleaved by plasmin. In the above report, the morphology of fibrinogen was observed under an electron microscope. The C-terminal region of each of the two Aα-chains in fibrinogen is bound to the central E domain under neutral condition. When a fibrinopeptide is cleaved from the Aα-chain through thrombin digestion, the C-terminal region of the Aα-chain bound to the E domain are dissociated. The dissociation results in conformation change in the C-terminal region of the Aα-chain. The monoclonal antibody of the present invention specifically recognizes this conformation-changed site.

The monoclonal antibody of the present invention may be produced through the following procedure.

A fibrin monomer or a soluble fibrin, which has been formed from fibrinogen, is preferably employed as an immunogen. Alternatively, only thrombin-treated fibrinogen or batroxobin-treated fibrinogen, which are not treated with plasmin, may also be employed. Fibrin monomers may be prepared through, for example, the method disclosed by U. SCHEEFERS-BORCHEL et al. [Proc. Natl. Acad. Sci. USA.

82, 7091 to 7095, 1985]. Specifically, a desAA fibrin monomer can be prepared through treating a fibrinogen solution with batroxobin and solubilizing the formed fibrin clot by use of urea or acid, whereas a desAABB fibrin monomer can be prepared through treating a fibrinogen solution with thrombin and solubilizing the formed fibrin clot by use of urea or acid. Alternatively, fibrinogen is treated with a very small amount of batroxobin or thrombin and the thus-formed solution, which is not a formed clot, may be employed without performing further treatments. Yet alternatively, there may be employed a C-terminal fragment of Aα-chain cleaved from fibrinogen through treatment with plasmin, or a synthesized polypeptide having the same sequence as a partial sequence of the C-terminal fragment of the Aα-chain. Preferably, the aforementioned 502-521 polypeptide is synthesized, and the synthetic peptide is employed.

No particular limitation is imposed on an animal used in immunization. Examples of the animal include mice and rats. Immunization can be performed through a conventional method. In an exemplified method, a suspension of an immunogen in a commonly employed buffer or physiological saline or a mixture of the immunogen and a replenisher such as complete Freund's adjuvant, is administered to an animal subcutaneously, intracutaneously, or intraperitoneally so as to perform primary immunization, and the immunization is repeated if needed. The administration dose of the immunogen is appropriately determined depending on the route of administration or the species of the animal, and in general, dose is preferably about 10 μg to 1 mg per administration.

Immunocytes used for cell fusion are preferably spleen cells collected on 3 to 4 days after final immunization. Myeloma cells to be fused with the immunocytes are preferably any known cell lines which have already been established. Examples of the cell lines include mouse cell lines such as NS1 (P3/NSI/I-Ag4-1) [Eur. J. Immunol. 6: 511-519 (1976)]; SP2/O—Ag14 [Nature 276: 269 (1978)]; P3-X63-Ag8.653 [J. Immunol. 123: 1548 (1979)]; and P3-X63-Ag8U.1 [Curr. Top. Microbiol. Immunol. 81:1 (1978)], and rat cell lines such as Y3-Ag1.2.3 [Nature 277: 131-133 (1979)]; and YB2/O (YB2/3HL/P2.G11.16Ag.20) [Methods Enzymol. 73B:1 (1981)].

In cell fusion, poly(ethylene glycol) (PEG), Sendai virus (HVJ) or the like which is conventionally employed can be used. Cell fusion may be performed according to any conventional methods. For example, to a mixed pellet of myeloma cells and immunocytes in an amount of approximately 1 to 10 times of that of the myeloma cells, poly(ethylene glycol) having an average molecular weight of 1,000 to 6,000 and a concentration of 30 to 60% is added dropwise, followed by mixing. The target hybridoma is selected using conventional culture medium such as an HAT medium (i.e., a medium containing hypoxanthine, aminopterin, and thymidine). After culturing in the HAT medium, the target hybridoma strain producing an antibody of interest may be selected and monocloned using a conventional limiting dilution method.

The target hybridoma strain producing antibody of interest can be obtained with ELISA, RIA or a similar assay. In the assay, the hybridoma strain can be obtained by selecting a strain producing an antibody which reacts specifically with soluble fibrin on which plasmin has not been acted but does not react with fibrinogen, or fibrin monomer-degradation product by plasmin or cross-linked fibrin-degradation product by plasmin.

Specifically, monoclonal antibodies contained in the supernatant of the culture medium are immobilized through an anti-mouse-IgG antibody or the like, and reacted with a sample containing soluble fibrin and fibrinogen. Next, an anti-fibrinogen antibody labeled with a labeling agent such as an enzyme is added to the reactant to thereby select a monoclonal antibody which reacts specifically with soluble fibrin but does not react with fibrinogen. Subsequently, a monoclonal antibody which does not react with fibrin fragments X, Y, or E which are fibrin-degradation products and cross-linked fibrin-degradation products (XDP) is selected. Through the above-described manner, a monoclonal antibody recognizing an epitope presenting in a fragment which is cleaved by plasmin is selected.

The monoclonal antibody may be produced according to a conventional method. For example, the hybridoma may be cultured to separate the antibody from culture supernatant. Alternatively, the hybridoma may be administered to a mammal compatible to the hybridoma, to collect the antibody from ascites.

When the monoclonal antibody of the present invention is applied to any of conventional immunological assay methods, a soluble fibrin in human body fluid on which plasmin has not acted can be specifically measured through the method.

When the assay is performed through the ELISA method, soluble fibrin can be measured through the following procedure employing purified soluble fibrin as a standard. Specifically, a diluted assay sample is added to an ELISA plate onto which the monoclonal antibody of the present invention has been immobilized, to thereby allow the sample to react with the antibody. Subsequently, it is further reacted with an anti-fibrinogen polyclonal antibody labeled with an enzyme. After coloration, soluble fibrin in the sample on which plasmin has not been acted can be specifically measured on the basis of change in absorbance. When the assay is performed through the LTIA method, soluble fibrin can be measured through the following procedure employing purified soluble fibrin as a standard. Specifically, latex particles serving as an insoluble carrier are sensitized by at least one monoclonal antibody of the invention, and a sample is brought into contact with the sensitized carrier, whereby antibody-sensitized latex particles are cross-linked together via soluble fibrin contained in the sample, and aggregated. The soluble fibrin can be specifically measured on the basis of change in degree of aggregation. No particular limitation is imposed on the assay sample, so long as it is a human body fluid containing soluble fibrin. Examples of the sample include blood and urine.

No particular limitation is imposed on the latex particles used for the antibody-sensitized latex particles in the assay methods such as the LTIA, so long as the particles are microparticles generally employed as a carrier in immunological agglutination or agglutination inhibition using latex aggregation. However, organic microparticles, which can be mass-produced on an industrial scale, are preferred. Examples of the material of such organic particles include a homopolymer and a copolymer of vinyl monomers such as styrene, vinyl chloride, acrylonitrile, vinyl acetate, acrylate ester, or methacrylate ester; and a butadiene copolymer such as styrene-butadiene copolymer and methyl methacrylate-butadiene copolymer. Alternatively, reactive organic microparticles, formed through bonding such organic microparticles to a functional group such as a carboxyl group, a primary amino group, a carbamoyl group, a hydroxyl group, or an aldehyde group, are preferably employed. Among the aforementioned latex particles, latex particles made of polystyrenes such as polystyrene and styrene-butadiene copolymer are preferred, since they exhibit excellent antigen- or antibody-adsorbability and ensure biological activity for a long period of time.

No particular limitation is imposed in the form of latex particles. However, the particles preferably have such a mean particle size that an agglutinate formed through agglutination between a protein present on the surfaces of the latex particles and an assay subject can be detected visually or optically. Preferably, the mean particle size is 0.02 to 1.6 μm, particularly preferably 0.03 to 0.5 μm.

No particular limitation is imposed on the method of sensitizing the latex particles with the monoclonal antibody of the present invention, and any known methods may be employed. Examples of the sensitization method include physical adsorption of the antibody onto the surfaces of the latex particles, and sensitization of the surfaces of the latex particles having a functional group via a covalent bond or through immunological binding.

In addition to the latex particles sensitized with the monoclonal antibody of the present invention, a stabilizer such as BSA or sucrose, or a preservative such as sodium azide may be used with a reagent for assaying soluble fibrin of the present invention. The reagent for soluble fibrin assay of the present invention may be further combined with a diluent, to thereby provide a latex aggregation test kit. The diluent may further optionally contain the aforementioned stabilizer or preservative.

EXAMPLES

The present invention will hereinafter be described in detail by way of examples, which should not be construed as limiting the invention thereto.

Example 1

Preparation of Monoclonal Antibody (1) Preparation of Hybridoma

Purified human fibrinogen dissolved in PBS was treated with batroxobin, to thereby form soluble fibrin serving as an immunogen. This immnogen and a complete Freund's adjuvant (GIBCO) were mixed at 1:1, to thereby prepare a 0.1 mg/0.1 mL emulsion. The emulsion was subcutaneously administered to 6-week-old female BALB/C mice six times at one-week intervals. Three days after final immunization, the spleen was extirpated from each mouse. Spleen cells collected from the extirpated spleen and myeloma cells SP2/O—Ag14 were mixed at 6:1, and they were fused in the presence of 50% polyethylene glycol 1540 (Wako Pure Chemical Industries, Ltd.). The thus-fused cells were suspended in a HAT medium such that the concentration of spleen cells was adjusted to $2.5 \times 10^6$/mL. The suspension was dispensed into a 96-well culture plate (Corning Incorporated) at 0.2 mL/well, followed by culturing at 37° C. in a 5% $CO_2$ incubator. After approximately two weeks, desired strains for production of an antibody against soluble fibrin were selected by examining culture supernatant in each well in which hybridoma had been grown using the ELISA method described hereinafter.

Firstly, IgGs contained in each culture supernatant were immobilized on a microplate (Nunc) using a goat anti-mouse IgG (Fc) antibody (The Jackson Laboratory). To the plate, soluble fibrin, fibrinogen, fibrins X, Y, and E, and cross-linked fibrin degraded products (XDP) were added to induce reaction with the IgGs. After a peroxidase-labeled anti-fibrinogen rabbit polyclonal antibody (DAKO) was added, the resultant product was allowed to develop color with a peroxidase substrate solution containing o-phenylenediamine (Tokyo Chemical Industry Co., Ltd.). The coloring was terminated through addition of 1.5N sulfuric acid. The degree of coloring was measured by means of a microplate reader (Abs. 492 nm), to thereby select strains which had exhibited high reactivity to soluble fibrin but no reactivity to fibrinogen, fibrins X, Y, and E, and cross-linked fibrin degradation products (XDP). The thus-obtained hybridoma was cloned through limiting dilution, to thereby establish a hybridoma producing an anti-soluble fibrin monoclonal antibody (J2-23). This hybridoma was deposited as FERM BP-10172 in National Institute of Advanced Industrial Science and technology, International Patent Organism Depositary (Central 6th, 1-1-1 Higashi, Tsukuba City, Ibaraki, 305-8566, Japan) on Dec. 3, 2004. Hereinafter, the anti-soluble fibrin monoclonal antibody secreted from the hybridoma (J2-23) is referred to as a "J2-23 antibody."

(2) Preparation of Monoclonal Antibody

To each of the 12-week old female BALB/C mice which were intraperitoneally injected pristane (0.5 mL) two weeks ago, the above-prepared hybridoma ($0.5 \times 10^6$ cells) was intraperitoneally injected to the mice. About 14 days after the administration of the hybridoma, ascites were collected and centrifuged, to thereby yield a supernatant. The supernatant was admixed with an equi-amount of an adsorption buffer (3 mol/L NaCl-1.5-mol/L Glycine-NaOH, pH 8.5), and the mixture was filtered. The resultant filtrate was passed through a protein A column (Pharmacia Corporation) which had been equilibrated with the adsorption buffer, to thereby adsorb the antibody onto the column. The adsorbed antibody was eluted from the column by use of a 0.1-mol/L citric acid buffer (pH 3.0), to thereby purify the anti-soluble fibrin monoclonal antibody (J2-23 antibody).

Example 2

Identification of Immunoglobulin Class and Specificity of Anti-Soluble Fibrin Monoclonal Antibody (J2-23 Antibody) (1)

Immunoglobulin class of J2-23 antibody was determined through ELISA (ZYMED). The antibody was found to have the immunoglobulin class of IgG1, κ light chain.

The J2-23 antibody was diluted with PBS to the concentration of 5 μg/mL. The diluted antibody was added to a 96-well ELISA plate (Nunc) at 50 μL/well and incubated overnight at 4° C. The plate was washed three times with PBS, and, subsequently, a blocking solution (PBS containing 1% BSA) was added at 100 μL/well, to thereby carry out blocking for one hour. After removal of the blocking solution, each of the antigens listed in Table 1 diluted by the blocking liquid was added at 50 μL/well, and the mixture was incubated for one hour at room temperature. The plate was washed three times with the blocking solution, and, subsequently, a peroxidase-labeled anti-fibrinogen rabbit polyclonal antibody was added, and the mixture was incubated for one hour at room temperature. The plate was washed three times with the blocking solution, and, subsequently, the peroxidase substrate solution prepared in Example 1 was added at 50 μL/well. After ten minutes, 1.5N sulfuric acid was added at 50 μL/well, and absorbance at 492 nm was measured.

Antigens in Table 1 were prepared as follows. Fibrinogen (hereinafter it is also referred to as Fbg) employed was prepared by further purifying purified fibrinogen (Sigma) through gel filtration. Each of a desAA fibrin monomer (hereinafter may be referred to as desAAFbn) and a desAABB fibrin monomer (hereinafter may be referred to as desAABBFbn) was prepared by treating purified Fbg with batroxobin or thrombin to form clots, followed by solubilizing the formed clots with acid. Each of a desAAFbn-Fbg complex and a desAABBFbn-Fbg complex was prepared by adding the acid-solubilized desAAFbn or desAABBFbn to an Fbg solution to induce complex formation, and separating polymer fraction from the mixture with gel filtration. Commercially available Fbg fragments X and Y (these products are of International Bio) were employed. Each of fibrin fragments X and Y was prepared through treatment of the Fbg fragment X or Y with thrombin. Commercially available Fbg fragment E, and fibrin fragment E, D dimer (DD) and D monomer (D) (these products are of International Bio) were employed. XDP containing DD/E were prepared by digesting a fibrin clot with plasmin, and separating the digested products with gel filtration to yield high molecular weight fraction.

The results of the experiment described above are shown in Table 1. In Table 1, "+" denotes occurrence of reaction and "–" denotes no occurrence, of reaction in sandwich ELISA.

TABLE 1

| Antigens | J2-23 antibody |
|---|---|
| Fibrinogen | – |
| desAA fibrin monomer | + |
| desAA fibrin-fibrinogen complex | + |
| desAABB fibrin monomer | + |
| desAABB fibrin-fibrinogen complex | + |
| Fibrinogen fragment X | – |
| Fibrin fragment X | – |
| Fibrinogen fragment Y | – |
| Fibrin fragment Y | – |
| Fibrinogen fragment E | – |
| Fibrin fragment E | – |
| XDP fraction containing DD/E | – |
| DD | – |
| D | – |

As is clear from Table 1, the monoclonal antibody of the present invention (J2-23 antibody) exhibits reactivity with, among various antigens in the solution, desAAFbn, desAAFbn-Fbg complex, desAABBFbn and desAABBFbn-Fbg complex, and no reactivity with untreated Fbg, fibrinogen-degradation products by plasmin (FbgDPs; i.e., fibrinogen fragment X, fibrinogen fragment Y, fibrinogen fragments E and D) and fibrin-degradation products by plasmin (FbnDPs; i.e., fibrin fragment X, fibrin fragment Y, fibrin fragment E, XDP fraction containing DD/E, and DD).

Example 3

Identification of Specificity of Anti-Soluble Fibrin Monoclonal Antibody (J2-23 Antibody) (2)

The antigens evaluated in Example 2 were separated with SDS-PAGE under non-reducing conditions, and transferred to a PVDF membrane. The membrane was blocked with PBST (PBS supplemented with 0.05% Tween 20) containing 3% skim milk for one hour, then reacted with the monoclonal antibody (J2-23 antibody; primary antibody) and peroxidase-labeled anti-mouse IgG antibody (secondary antibody; Biosource International). After washing the PVDF membrane with PBST, diaminobenzidine was added as a substrate, to thereby allow color development. As a result, the J2-23 antibody was found to react not only with desAAFbn and desAABBFbn but also with Fbg, and to exhibit no reactivity with FbgDPs. Similar procedure to that described above was performed using Fbg further treated under reducing conditions, showing that the antibody reacted intensely with the Aα chain of Fbg (FIG. 1).

Through the analysis, the epitope for the monoclonal antibody of the present invention (J2-23 antibody) was found not to appear in a non-denatured Fbg in test solution but to appear on the Aα chain of denatured Fbg. Since the J2-23 antibody does not react with FbgDPs, the reaction site has been proven to be present in a fragment cleaved from soluble fibrin by plasmin.

Example 4

Epitope Analysis of Anti-Soluble Fibrin Monoclonal Antibody (J2-23 Antibody) (1)

On the basis of the finding obtained in Example 3, the position of the epitope on the Aα chain was identified through the following procedure. Firstly, purified Fbg was dissolved in 10 mmol/L Tris buffer (pH 8.0) so as to form a solution having a final concentration of 10 mg/mL, and plasmin (Chromogenics) was added to the solution so as to attain a final concentration of 0.2 units/mL. Fbg was digested at 37° C. for 30 minutes. Subsequently, aprotinin (Mitsubishi Pharma Corporation) was added to the digestant so as to attain a final concentration of 500 units/mL, whereby plasmin was inactivated. The digestant was reduced, and the reduction product was subjected to separation with 15 to 25% SDS-PAGE and the resultant matter was transferred to PVDF. CBB staining was performed after the transfer. And immunoblotting was independently performed after the transfer by use of the monoclonal antibody of the present invention (J2-23 antibody) in a manner similar to that of Example 3.

Figure 2:
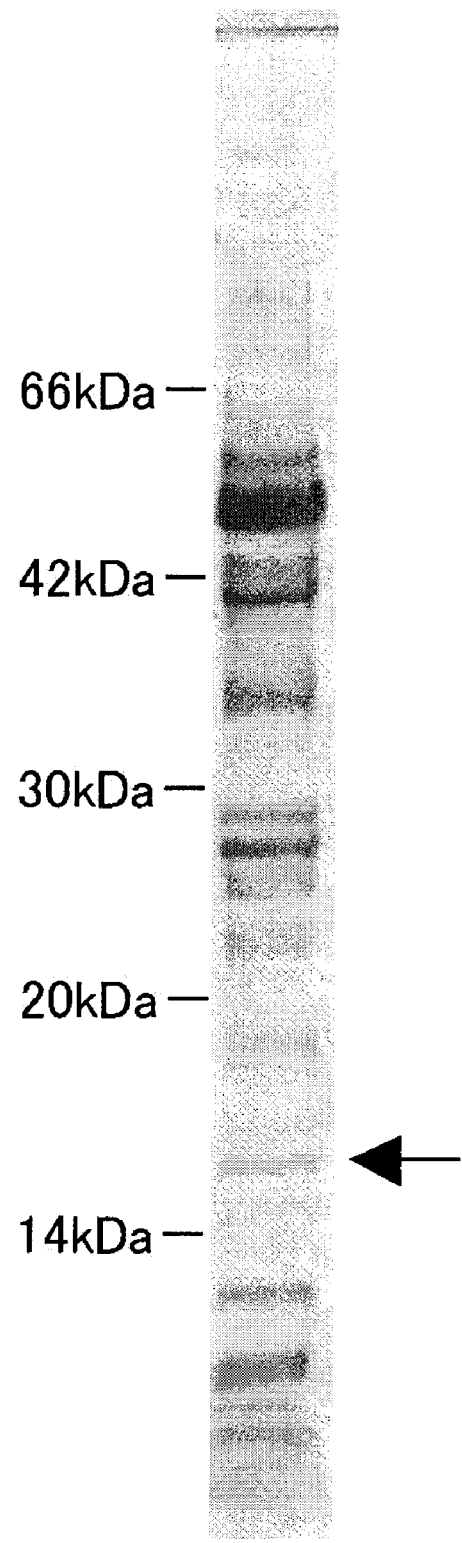
[FIG. 2] An electrophoresis image showing reactive digestion fragments (protein-stained with CBB), which was obtained by Western blotting analysis carried out in Example 4 for reactivity of J2-23 antibody with plasmin-digestion fragments of fibrinogen.

As a result, a digested fragment (about 16 kDa) having reactivity with the J2-23 antibody was observed (a band indicated by the arrow in FIG. 2). The digested fragment stained by CBB was removed, and the N-terminal amino acid sequence was analyzed. The sequence was found to be a TGKEKVTS (SEQ ID NO: 3) with the N terminal end corresponding to the 425th amino acid residue of the Aα chain of Fbg.

Since the sequence is included in a fragment which is cleaved from Fbg when the Fbg is transformed to Fbg-X through plasmin digestion, the epitope for the monoclonal antibody of the present invention has been proven to be present on the Aα chain of Fbg and in the C-terminal region of the Aα chain cleaved through plasmin digestion. Further, the epitope for the antibody of the present invention has been proven to be present on the downstream region of the 425th amino acid of the Aα chain in the plasmin-digested fragment. Hitherto, there has never been known an antibody against a soluble fibrin, which exhibits reactivity with a C-terminal fragment of the Aα chain formed through plasmin digestion. Therefore, the antibody of the invention has been found to be novel.

Example 5

Epitope Analysis of Anti-Soluble Fibrin Monoclonal Antibody (J2-23 Antibody) (2)

On the basis of the finding obtained in Example 4, the position of the epitope on the Aα chain was further analyzed through the following procedure.

Through the method by Doolittle et al. (Biochemistry 1977, 16: 1703), an Aα chain was isolated from Fbg and purified. The purified Aα chain was digested with Endoproteinase Asp-N (Sigma), and immunoblotting was performed in a manner similar to that of Example 4.

As a result, a digested fragment (7 to 8 kDa) was observed, and the N-terminal amino acid sequence of the digested fragment was analyzed. Through analysis, the sequence was found to be a DTAST (SEQ ID NO: 4) with the N terminal corresponding to the 502nd amino acid on the Aα chain of Fbg. Considering the molecular weight of the digested fragment and the fact that a cleaving site by the Asp-N is present on the side of the amino group of aspartic acid, the fragment is considered as the peptide of the 502nd to 573rd amino acid residues of the Aα chain.

Subsequently, 6 peptides (starting from the 502nd amino acid: AA502-521 (SEQ ID NO: 5), AA512-531 (SEQ ID NO: 6), AA522-541 (SEQ ID NO: 7), AA532-551 (SEQ ID NO: 8), AA542-561 (SEQ ID NO: 9), and AA552-571 (SEQ ID NO: 10)) included in the amino acid sequence of the above digested fragment were synthesized, and the epitope for the monoclonal antibody of the present invention (J2-23 antibody) was identified more precisely according to the following procedure.

Firstly, a goat anti-mouse IgG (Fc) antibody was diluted with PBS to the concentration of 5 μg/mL. The antibody solution was added to a micro-plate at 50 μL/well and incubated overnight at 4° C. The plate was washed three times with PBST (PBS supplemented with 0.05% Tween 20), to which a blocking solution (BSA-PBST) was added at 100 μL/well, and the mixture was incubated for one hour at room temperature. After washing three times with PBST, the monoclonal antibody of the present invention (J2-23 antibody) was diluted with BSA-PBST to a concentration of 0.2 μg/mL, and added to the micro-plate at 50 μL/well. The mixture was incubated for one hour at room temperature. After washing three times with PBST, each of the above-synthesized peptides diluted with BSA-PBST to 0 to 100 μg/mL was added to the micro-plate at 25 μL/well, and the mixture was incubated at room temperature for 30 minutes. Subsequently, soluble fibrin (prepared in Example 6 mentioned hereinbelow) was diluted with BSA-PBST to 1 μg/mL, and added to the micro-plate at 25 μL/well, followed by incubation at room temperature for one hour. After washing three times with PBST, an HRP-rabbit anti-human fibrinogen antibody (DAKO) diluted to 5,000-fold with BSA-PBST was added to the micro-plate at 50 μL/well, followed by incubation at room temperature for one hour. After washing three times with PBST, the peroxidase substrate solution prepared in Example 1 was added to the micro-plate at 50 μL/well. Ten minutes after the addition of the substrate solution, 1.5N sulfuric acid was added at 50 μL/well, and absorbance at 492 nm was measured.

Figure 3:
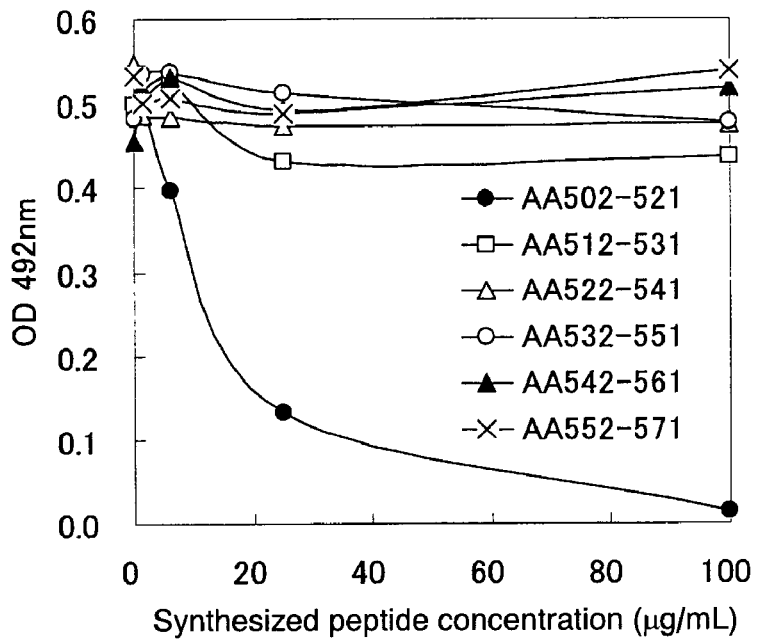
[FIG. 3] A graph showing competitive inhibition between six synthetic peptides and the monoclonal antibody of the present invention.

The results are shown in FIG. 3. Among the six synthesized peptides, only AA502-521 exhibited competitive inhibition. Therefore, the epitope recognized by the monoclonal antibody of the present invention (J2-23 antibody) has been proven to be an amino acid sequence of 502nd to 521st on the Aα chain of Fbg. This result indicates that a conformation change is generated in the Aα-chain C-terminal region, at least in the vicinity of the 502nd to 521st amino acid residues, of the soluble fibrin formed from Fbg by thrombin. Therefore, the monoclonal antibody of the present invention (J2-23 antibody) is a soluble fibrin-specific antibody which specifically recognizes a site with the conformation change.

Example 6

Assay for measuring Soluble Fibrin Employing Latex Turbidometric Immunoassay (LTIA)

(1) Preparation of Antibody-Sensitized Latex

A monoclonal antibody (J2-23 antibody) was diluted with 20 mmol/L Tris-HCl buffer (pH7.5) to 0.7 mg/mL. The antibody solution was admixed with an equiamount of a 1% latex solution (particle size: 0.2 μm, Sekisui Chem. Co., Ltd.), and the mixture was stirred at 4° C. for about two hours. Subsequently, an equiamount of 1% BSA was added to the mixture, followed by stirring for one hour. The product was centrifuged (100,000×g, 5 min). The precipitated latex was suspended in 5 mmol/L MOPS (pH 7.0) containing 0.5% BSA, to thereby prepare an antibody-sensitized latex.

(2) Preparation of Soluble Fibrin

In a manner similar to that of Example 2, acid-soluble desAAFbn and desAABBFbn were prepared. Each fibrin monomer was added to human citrated plasma to a final concentration of 0 to 50 μg/mL, to thereby prepare soluble fibrin.

(3) Assay for Measuring Soluble Fibrin

Figure 4:
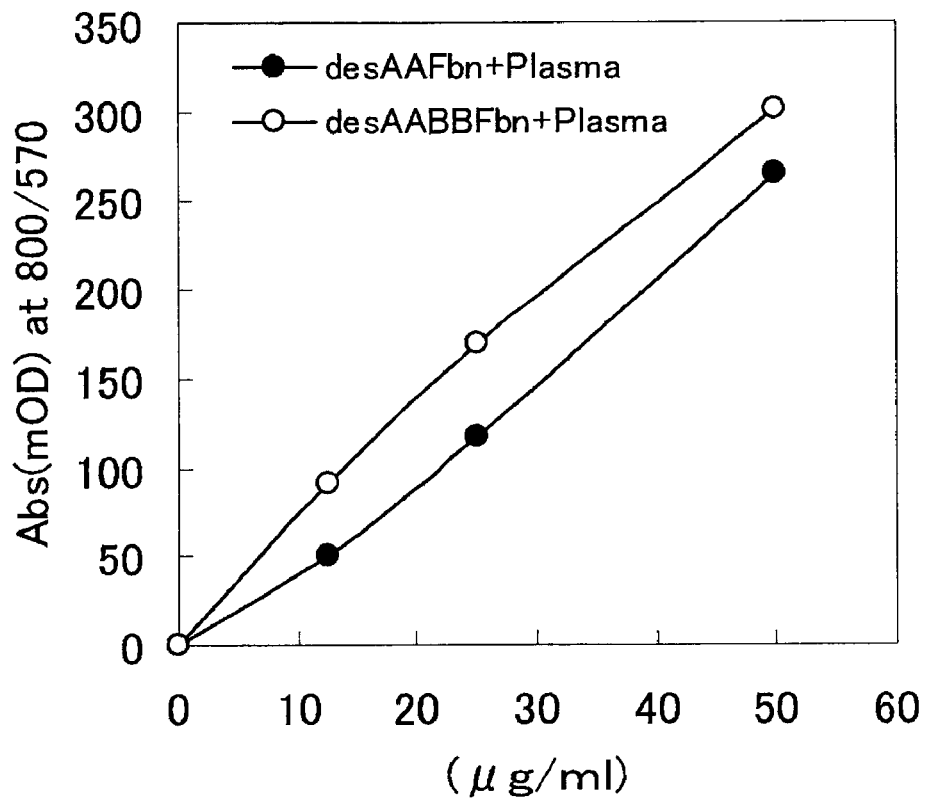
[FIG. 4] A graph showing reactivity of soluble fibrin with LTIA reagent investigated in Example 6.

A 30 mmol/L Tris-HCl buffer (pH 8.5) containing 0.4% BSA and 0.5 mol/L sodium chloride (Reagent 1) was prepared. The assay was performed using Reagent 1 and the antibody-sensitized latex prepared above (Reagent 2) by means of a biochemical autoanalyzer (Hitachi, Model 7170). Specifically, to each reaction cell in the autoanalyzer maintained at 37° C., each of the above-prepared soluble fibrins (3 μL) and the Reagent 1 (100 μL) were added. Five minutes after the addition of Reagent 1, Reagent 2 (100 μL) was added to cause antigen-antibody reaction for 5 minutes. A change in absorbance at a main wavelength of 570 nm and a sub wavelength of 800 nm was measured before and after reaction (between point 18 and point 34) (FIG. 4). Absorbance was changed with the concentration of each of the desAAFbn and desAABBFbn which had been added, which indicating that soluble fibrin level in blood can be measured using the monoclonal antibody of the present invention.

The invention claimed is:

1. A hybridoma deposited as FERM BP-10172.

2. An isolated or purified monoclonal antibody that is J2-23 produced by a hybridoma deposited as FERM BP-10172.

3. An isolated or purified monoclonal antibody that binds to amino acid residues 502-521 of SEQ ID NO: 1 and to soluble human monomeric fibrin, but which does not bind to human fibrinogen.

4. An isolated or purified monoclonal antibody that specifically binds to a soluble fibrin monomer and specifically binds to residues 502-521 of SEQ ID NO: 1.

5. The monoclonal antibody of claim 4, wherein a site recognized by the antibody is present in a C-terminal fragment of an Aα-chain of fibrinogen, and wherein the fragment is cleaved from fibrinogen when fibrinogen is transformed to a fibrinogen X through plasmin digestion.

6. The monoclonal antibody of claim 4, wherein a site recognized by the antibody is present in a peptide having a molecular weight of about 16 kDa, and wherein an N-terminal end of the peptide corresponds to the 425th amino acid residue of an Aα-chain of the fibrinogen.

7. The monoclonal antibody of claim 4, wherein a site recognized by the antibody is a peptide having an amino acid sequence consisting of the 502nd to 521st amino acid residues of Aα-chain of fibrinogen.

8. The monoclonal antibody of claim 4 that binds to a soluble fibrin that is a fibrin monomer complex selected from the group consisting of a fibrin polymer, a fibrin monomer-fibrinogen complex, and a fibrin monomer-FDP complex.

9. The monoclonal antibody of claim 4 that binds to a soluble fibrin that is a fibrin monomer or a fibrin monomer complex.

10. The monoclonal antibody of claim 9 that does not specifically bind to fibrinogen, a fibrin monomer-degradation product by plasmin, or a cross-linked fibrin degradation product by plasmin.

11. The monoclonal antibody of claim 9, which binds to a soluble fibrin that is a desAA fibrin monomer.

12. The monoclonal antibody of claim 9, which binds to a soluble fibrin that is a desAABB fibrin monomer.

13. A composition suitable as a reagent in an assay for measuring a soluble fibrin, which comprises the monoclonal antibody of claim 4.

14. A method for detecting soluble fibrin in a sample comprising:

contacting a sample with the monoclonal antibody of claim 4 under conditions suitable for complex formation between the monoclonal antibody and soluble fibrin, and detecting or measuring the amount of complex formation, wherein complex formation or the amount of complex formation is indicative of the presence of soluble fibrin or indicative of the amount of soluble fibrin in said sample.

15. The method of claim 14, wherein the monoclonal antibody has been immobilized on an insoluble carrier.

16. A method for evaluating hypercoagulability in a test sample, which comprises:

contacting a sample with the monoclonal antibody of claim 4 under conditions suitable for complex formation between the monoclonal antibody and soluble fibrin, and measuring the amount of complex formation, wherein the amount of complex formation is indicative of the amount of soluble fibrin in the sample on which plasmin has not acted and is indicative of the hypercoagulability of said sample.

17. An isolated or purified monoclonal antibody that specifically binds to a soluble fibrin that is desAA fibrin monomer or desAABB fibrin monomer and specifically recognizes a conformation-changed site newly occurred in a C-terminal region of an Aα-chain of soluble fibrin formed through thrombin digestion of a fibrinogen and present within positions 502 to 521 of SEQ ID NO: 1.

\* \* \* \* \*

SEQUENCE LISTING

```
<160> NUMBER OF SEQ ID NOS: 10

<210> SEQ ID NO 1
<211> LENGTH: 610
<212> TYPE: PRT
<213> ORGANISM: human

<400> SEQUENCE: 1

Ala Asp Ser Gly Glu Gly Asp Phe Leu Ala Glu Gly Gly Gly Val Arg
1               5                   10                  15
```

-continued

```
Gly Pro Arg Val Val Glu Arg His Gln Ser Ala Cys Lys Asp Ser Asp
            20                  25                  30

Trp Pro Phe Cys Ser Asp Glu Asp Trp Asn Tyr Lys Cys Pro Ser Gly
            35                  40                  45

Cys Arg Met Lys Gly Leu Ile Asp Glu Val Asn Gln Asp Phe Thr Asn
50                  55                  60

Arg Ile Asn Lys Leu Lys Asn Ser Leu Phe Glu Tyr Gln Lys Asn Asn
65                  70                  75                  80

Lys Asp Ser His Ser Leu Thr Thr Met Ile Met Glu Ile Leu Arg Gly
                85                  90                  95

Asp Phe Ser Ser Ala Asn Asn Arg Asp Asn Thr Tyr Asn Arg Val Ser
            100                 105                 110

Glu Asp Leu Arg Ser Arg Ile Glu Val Leu Lys Arg Lys Val Ile Gln
            115                 120                 125

Lys Val Gln His Ile Gln Leu Leu Gln Lys Asn Val Arg Ala Gln Leu
130                 135                 140

Val Asp Met Lys Arg Leu Glu Val Asp Ile Asp Ile Lys Ile Arg Ser
145                 150                 155                 160

Cys Arg Gly Ser Cys Ser Arg Ala Leu Ala Arg Glu Val Asp Leu Lys
                165                 170                 175

Asn Tyr Glu Asp Gln Gln Lys Gln Leu Glu Gln Val Ile Ala Lys Asp
            180                 185                 190

Leu Leu Pro Ser Arg Asp Arg Gln His Leu Pro Leu Ile Lys Met Lys
            195                 200                 205

Pro Val Pro Asn Leu Val Pro Gly Asn Phe Lys Ser Gln Leu Gln Lys
210                 215                 220

Val Pro Pro Glu Trp Lys Ala Leu Thr Asp Met Pro Gln Met Arg Met
225                 230                 235                 240

Glu Leu Glu Arg Pro Gly Gly Asn Glu Ile Thr Arg Gly Gly Ser Thr
                245                 250                 255

Ser Tyr Gly Thr Gly Ser Glu Thr Glu Ser Pro Arg Asn Pro Ser Ser
            260                 265                 270

Ala Gly Ser Trp Asn Ser Gly Ser Ser Gly Pro Gly Ser Thr Gly Asn
            275                 280                 285

Arg Asn Pro Gly Ser Ser Gly Thr Gly Ser Gly Ala Thr Trp Lys Pro
290                 295                 300

Gly Ser Ser Gly Pro Gly Ser Thr Gly Ser Trp Asn Ser Gly Ser Ser
305                 310                 315                 320

Gly Thr Gly Ser Thr Gly Asn Gln Asn Pro Gly Ser Pro Arg Pro Gly
                325                 330                 335

Ser Thr Gly Thr Trp Asn Pro Gly Ser Ser Glu Arg Gly Ser Ala Gly
            340                 345                 350

His Trp Thr Ser Glu Ser Ser Val Ser Gly Ser Thr Gly Gln Trp His
            355                 360                 365

Ser Glu Ser Gly Ser Phe Arg Pro Asp Ser Pro Gly Ser Gly Asn Ala
            370                 375                 380

Arg Pro Asn Asp Pro Asn Trp Gly Thr Phe Glu Glu Val Ser Gly Asn
385                 390                 395                 400

Val Ser Pro Gly Thr Arg Arg Glu Tyr His Thr Glu Lys Leu Tyr Thr
                405                 410                 415

Ser Lys Gly Asp Lys Glu Leu Arg Thr Gly Lys Glu Lys Val Thr Ser
            420                 425                 430
```

```
Gly Ser Thr Thr Thr Thr Arg Arg Ser Cys Ser Lys Thr Val Thr Lys
            435                 440                 445

Thr Val Ile Gly Pro Asp Gly His Lys Glu Val Thr Lys Glu Val Val
    450                 455                 460

Thr Ser Glu Asp Gly Ser Asp Cys Pro Glu Ala Met Asp Leu Gly Thr
465                 470                 475                 480

Leu Ser Gly Ile Gly Thr Leu Asp Gly Phe Arg His Arg His Pro Asp
                485                 490                 495

Glu Ala Ala Phe Phe Asp Thr Ala Ser Thr Gly Lys Thr Phe Pro Gly
                500                 505                 510

Phe Phe Ser Pro Met Leu Gly Glu Phe Val Ser Glu Thr Glu Ser Arg
            515                 520                 525

Gly Ser Glu Ser Gly Ile Phe Thr Asn Thr Lys Glu Ser Ser Ser His
    530                 535                 540

His Pro Gly Ile Ala Glu Phe Pro Ser Arg Gly Lys Ser Ser Ser Tyr
545                 550                 555                 560

Ser Lys Gln Phe Thr Ser Ser Thr Ser Tyr Asn Arg Gly Asp Ser Thr
                565                 570                 575

Phe Glu Ser Lys Ser Tyr Lys Met Ala Asp Glu Ala Gly Ser Glu Ala
                580                 585                 590

Asp His Glu Gly Thr His Ser Thr Lys Arg Gly His Ala Lys Ser Arg
            595                 600                 605

Pro Val
    610

<210> SEQ ID NO 2
<211> LENGTH: 6
<212> TYPE: PRT
<213> ORGANISM: Artificial
<220> FEATURE:
<223> OTHER INFORMATION: Synthetic hexapeptide

<400> SEQUENCE: 2

Gly Pro Arg Val Val Glu
1               5

<210> SEQ ID NO 3
<211> LENGTH: 8
<212> TYPE: PRT
<213> ORGANISM: homo sapiens
<220> FEATURE:
<221> NAME/KEY: MISC_FEATURE
<222> LOCATION: (1)..(8)
<223> OTHER INFORMATION: N-terminal end corresponding to 425th amino
      acid residue of A-alpha chain of fibrinogen.

<400> SEQUENCE: 3

Thr Gly Lys Glu Lys Val Thr Ser
1               5

<210> SEQ ID NO 4
<211> LENGTH: 5
<212> TYPE: PRT
<213> ORGANISM: homo sapiens
<220> FEATURE:
<221> NAME/KEY: MISC_FEATURE
<222> LOCATION: (1)..(5)
<223> OTHER INFORMATION: N-terminal corresponding to the 502nd amino
      acid on the A-alpha chain of fibrinogen.

<400> SEQUENCE: 4

Asp Thr Ala Ser Thr
```

-continued

```
1               5

<210> SEQ ID NO 5
<211> LENGTH: 20
<212> TYPE: PRT
<213> ORGANISM: Artificial
<220> FEATURE:
<223> OTHER INFORMATION: Synthetic AA502-521

<400> SEQUENCE: 5

Asp Thr Ala Ser Thr Gly Lys Thr Phe Pro Gly Phe Phe Ser Pro Met
1               5                   10                  15

Leu Gly Glu Phe
            20

<210> SEQ ID NO 6
<211> LENGTH: 20
<212> TYPE: PRT
<213> ORGANISM: Artificial
<220> FEATURE:
<223> OTHER INFORMATION: Synthetic AA512-531

<400> SEQUENCE: 6

Gly Phe Phe Ser Pro Met Leu Gly Glu Phe Val Ser Glu Thr Glu Ser
1               5                   10                  15

Arg Gly Ser Glu
            20

<210> SEQ ID NO 7
<211> LENGTH: 20
<212> TYPE: PRT
<213> ORGANISM: Artificial
<220> FEATURE:
<223> OTHER INFORMATION: Synthetic AA522-541

<400> SEQUENCE: 7

Val Ser Glu Thr Glu Ser Arg Gly Ser Glu Ser Gly Ile Phe Thr Asn
1               5                   10                  15

Thr Lys Glu Ser
            20

<210> SEQ ID NO 8
<211> LENGTH: 20
<212> TYPE: PRT
<213> ORGANISM: Artificial
<220> FEATURE:
<223> OTHER INFORMATION: Synthetic AA532-551

<400> SEQUENCE: 8

Ser Gly Ile Phe Thr Asn Thr Lys Glu Ser Ser Ser His His Pro Gly
1               5                   10                  15

Ile Ala Glu Phe
            20

<210> SEQ ID NO 9
<211> LENGTH: 20
<212> TYPE: PRT
<213> ORGANISM: Artificial
<220> FEATURE:
<223> OTHER INFORMATION: Synthetic AA542-561

<400> SEQUENCE: 9

Ser Ser His His Pro Gly Ile Ala Glu Phe Pro Ser Arg Gly Lys Ser
1               5                   10                  15
```

```
Ser Ser Tyr Ser
            20

<210> SEQ ID NO 10
<211> LENGTH: 20
<212> TYPE: PRT
<213> ORGANISM: Artificial
<220> FEATURE:
<223> OTHER INFORMATION: Synthetic AA552-571

<400> SEQUENCE: 10

Pro Ser Arg Gly Lys Ser Ser Ser Tyr Ser Lys Gln Phe Thr Ser Ser
1               5                   10                  15

Thr Ser Tyr Asn
            20
```